(12) United States Patent
Lee et al.

(10) Patent No.: US 11,544,429 B2
(45) Date of Patent: Jan. 3, 2023

(54) APPARATUS AND METHOD FOR PREDICTING DEFORMATION TEMPERATURE OF COAL USING PREDICTIVE MODEL

(71) Applicant: DOOSAN ENERBILITY CO., LTD., Changwon-si (KR)

(72) Inventors: Jung Min Lee, Seoul (KR); Byoung Hwa Lee, Busan (KR)

(73) Assignee: DOOSAN ENERBILITY CO., LTD., Changwon (KR)

( * ) Notice: Subject to any disclaimer, the term of this patent is extended or adjusted under 35 U.S.C. 154(b) by 605 days.

(21) Appl. No.: 16/698,948

(22) Filed: Nov. 27, 2019

(65) Prior Publication Data

US 2020/0184132 A1 Jun. 11, 2020

(30) Foreign Application Priority Data

Dec. 7, 2018 (KR) .................. 10-2018-0157446

(51) Int. Cl.
*G06F 30/27* (2020.01)
*G01N 33/22* (2006.01)
(Continued)

(52) U.S. Cl.
CPC .......... *G06F 30/27* (2020.01); *G01N 33/222* (2013.01); *G06N 20/00* (2019.01); *G06F 2119/08* (2020.01)

(58) Field of Classification Search
CPC ................. G06F 30/27; G06F 2119/08; G01N 33/222; G06N 20/00
See application file for complete search history.

(56) References Cited

U.S. PATENT DOCUMENTS

| 2009/0125144 A1* | 5/2009 | Riley | ................ G01N 31/12 422/78 |
| 2011/0071788 A1* | 3/2011 | Riley | ................ G01N 31/12 702/179 |

(Continued)

FOREIGN PATENT DOCUMENTS

KR 20170074524 A 6/2017

OTHER PUBLICATIONS

"Prediction of coal ash fusion temperatures using computational intelligence based models", Sanjeev S. Tambe, Makarand Naniwadekar, Shishir Tiwary, Ashis Muklerjee, Tarit Baran Das, CrossMark, Sep. 19, 2018.*

(Continued)

*Primary Examiner* — Nha T Nguyen
(74) *Attorney, Agent, or Firm* — Harvest IP Law LLP

(57) ABSTRACT

An apparatus and method predict an initial deformation temperature of coal without an additional test by using a predictive model. The apparatus includes a parameter extractor configured to analyze characteristics of test coal and to extract parameters of the test coal based on the test coal characteristic analysis; a temperature analyzer configured to analyze an initial deformation temperature (IDT) of the test coal; a modeler configured to derive an IDT predictive model for predicting the test coal IDT using the extracted parameters of the test coal and the test coal IDT; and a predictor configured to predict an initial deformation temperature (IDT) of target coal to be supplied to the coal-fired power plant by substituting parameters of the target coal into the IDT predictive model. The test coal characteristics are analyzed by ash component analysis, elementary analysis, industrial analysis, or calorific value analysis.

19 Claims, 7 Drawing Sheets

(51) Int. Cl.
  *G06N 20/00*   (2019.01)
  *G06F 119/08*  (2020.01)

(56) References Cited

U.S. PATENT DOCUMENTS

2018/0073724 A1* 3/2018 Kim ...................... F01K 13/003
2020/0184132 A1* 6/2020 Lee ...................... G01N 33/222

OTHER PUBLICATIONS

MATEC Web of Conferences 40, 05010.
SISEST 2009—RUSNAS PEBT(Indonesia Student Mining Competition).

* cited by examiner

APPARATUS AND METHOD FOR PREDICTING DEFORMATION TEMPERATURE OF COAL USING PREDICTIVE MODEL

CROSS REFERENCE TO RELATED APPLICATION

The present application claims priority to Korean Patent Application No. 10-2018-0157446, filed on Dec. 7, 2018, the entire contents of which are incorporated herein for all purposes by this reference.

BACKGROUND OF THE INVENTION

Field of the Invention

The present disclosure relates to an apparatus and method for predicting an initial deformation temperature (IDT) of coal using a predictive model. More specifically, the present disclosure relates to an apparatus and method whereby coal IDT is predicted by deriving an IDT predictive model and putting the characteristics of coal into the IDT predictive model to predict the initial deformation temperature without a separate test.

Description of the Background Art

Generally, in coal-fired power plants, coal is crushed and the crushed coal is injected into a boiler. Slagging occurs when coal burned in the boiler is ashed and accumulates in a pipe.

The coal burned in a coal-fired power plant may include more than one type of coal, such that various types of coal are burned while mixed together (blended) for cost reduction purposes. The component ratio of blended coal in a coal-fired power plant is determined and consumed (burned) at a regular rate. After a period of time, the boiler is resupplied with additional coal, i.e., the coal blend.

SUMMARY OF THE INVENTION

Accordingly, the present invention has been made keeping in mind the above problems occurring in the related art. An object of the present invention is to provide an apparatus and method whereby an initial deformation temperature (IDT) according to characteristics of coal is predicted by deriving an IDT predictive model and putting (substituting) the characteristics of coal into the IDT predictive model to predict the initial deformation temperature without a separate test.

In addition to the above-mentioned technical task of the present disclosure, other features and advantages of the present disclosure will be described below, or from such description, will be clearly understood by those skilled in the art.

According to an aspect of the present disclosure, there is provided an apparatus for predicting an initial deformation temperature (IDT) of coal consumed in a coal-fired power plant. The apparatus may include a parameter extractor configured to analyze characteristics of test coal and to extract parameters of the test coal based on the test coal characteristic analysis; a temperature analyzer configured to analyze an initial deformation temperature (IDT) of the test coal; a modeler configured to derive an IDT predictive model for predicting the test coal IDT using the extracted parameters of the test coal and the test coal IDT; and a predictor configured to predict an initial deformation temperature (IDT) of target coal to be supplied to the coal-fired power plant by substituting parameters of the target coal into the IDT predictive model.

According to another aspect of the present disclosure, there is provided a method of predicting an initial deformation temperature (IDT) of coal consumed in a coal-fired power plant. The method may include analyzing characteristics of test coal; extracting parameters of the test coal based on the test coal characteristic analysis; analyzing an initial deformation temperature (IDT) of the test coal; deriving an IDT predictive model for predicting the test coal IDT using the extracted parameters of the test coal and the test coal IDT; and predicting an initial deformation temperature (IDT) of target coal to be supplied to the coal-fired power plant by using parameters of the target coal in the IDT predictive model.

According to the present disclosure, the parameter extractor may be further configured to analyze the characteristics of the test coal through one of ash component analysis, elementary analysis, industrial analysis, and calorific value analysis. Here, the parameters of the test coal extracted through the ash component analysis may relate to a content of at least one of $SiO_2$, $Al_2O_3$, $CaO$, $MgO$, $Na_2O$, $K_2O$, $TiO_2$, and $SO_3$.

The parameter extractor may be further configured to generate a derivative parameter by combining the plurality of extracted parameters of the test coal depending on a correlation with the test coal IDT, and the modeler may be further configured to derive the IDT predictive model by using the parameters of the test coal, the test coal IDT, and the derivative parameters. The parameter extractor may be further configured to generate the derivative parameter as a sum of $SiO_2$ content and $Al_2O_3$ content, as a sum of $CaO$ content and $MgO$ content, or as a sum of contents of basic oxides.

The modeler may be further configured to model the parameters of the test coal and the test coal IDT through machine learning.

The predictor may be further configured to analyze the characteristics of the target coal and to extract the parameters of the target coal based on the target coal characteristic analysis.

According to another aspect of the present disclosure, the above method may be implemented by a computer readable storage medium storing a computer program comprising instructions for performing the method.

According to the present disclosure, the apparatus and method may predict coal IDT without an additional test by using the IDT predictive model.

Further, according to the present disclosure, the apparatus and method may predict coal IDT through machine learning, thereby obtaining accurate results in less time and with less cost, compared to an offline test.

In addition, other features and advantages of the present disclosure may be newly understood through the embodiments of the present disclosure.

DETAILED DESCRIPTION OF THE INVENTION

Figure 1:
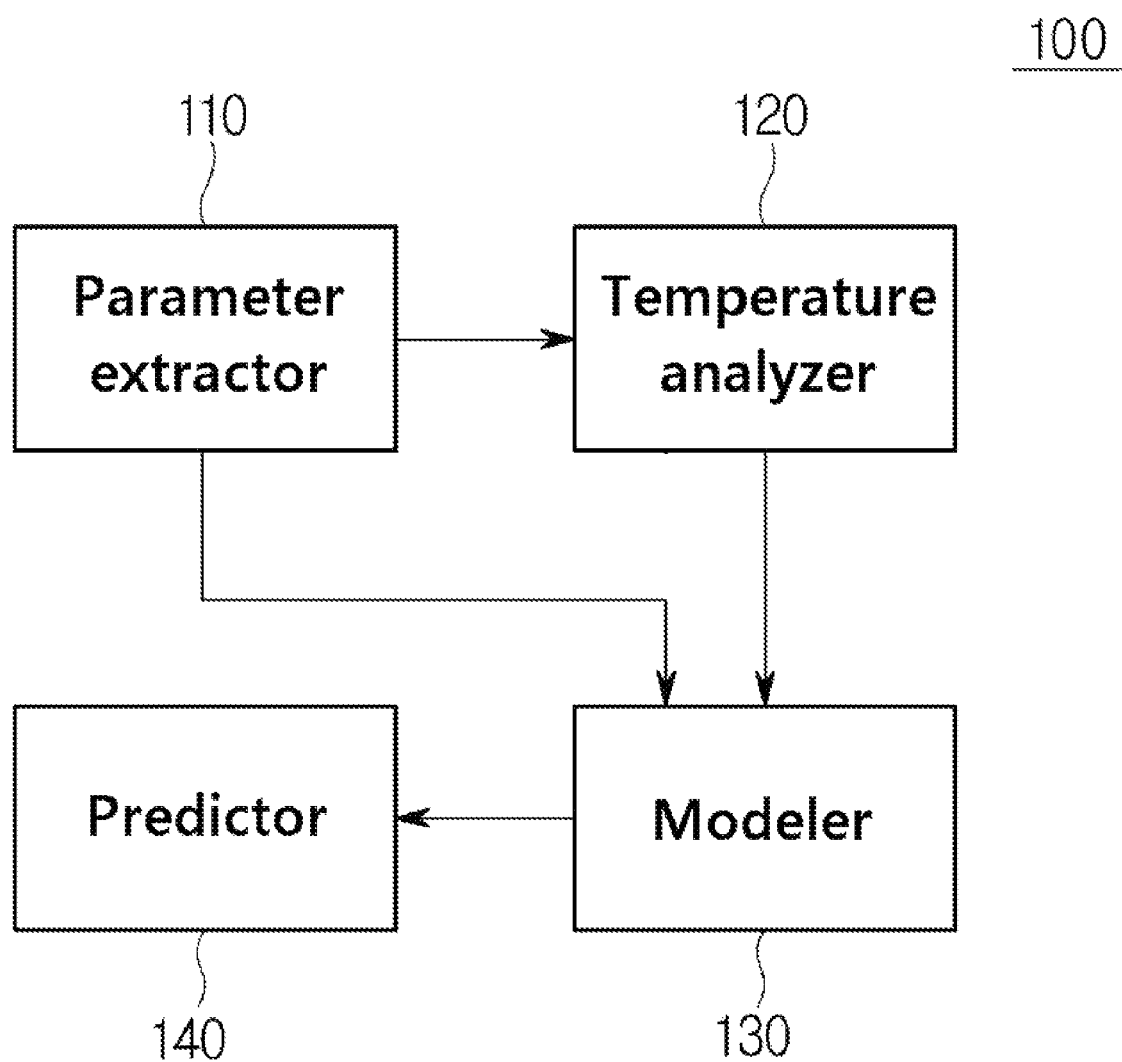
FIG. 1 is a block diagram of an apparatus for predicting initial deformation temperature of coal according to an embodiment of the present disclosure.

Parts not related to the description are omitted in order to clearly describe the present disclosure, and like reference numerals designate like elements throughout the specification.

The terminology used herein is for the purpose of describing particular embodiments only and is not intended to be limiting of the disclosure. As used herein, the singular forms "a", "an", and "the" include plural forms as well, unless the context clearly indicates otherwise. It will be further understood that the terms "comprises" and/or "comprising", or "includes" and/or "including" when used in this specification, specify the presence of stated features, regions, integers, steps, operations, elements and/or components, but do not preclude the presence or addition of one or more other features, regions, integers, steps, operations, elements and/or components.

Hereinafter, exemplary embodiments of the present disclosure will be described in detail with reference to the accompanying drawings so that those skilled in the art may easily implement the present disclosure. However, the present disclosure is not limited to the disclosed embodiments, but may be implemented into various different forms.

Coal is crushed and the crushed coal is injected into a boiler of a coal-fired power plant. Slagging occurs when coal burned in the boiler is ashed and accumulates in a pipe.

The coal burned in a coal-fired power plant may include more than one type of coal, such that various types of coal are burned while mixed together (blended) for cost reduction purposes. Mixed coal reduces the efficiency of the power plant, hinders deterioration management, and increases the incidence of slagging. Therefore, it is important to analyze the initial deformation temperature (IDT) of coal when slagging occurs.

Meanwhile, the component ratio of blended coal in a coal-fired power plant is determined and consumed (burned) at a regular rate. After a period of time, when the boiler is to be resupplied with additional coal, i.e., the coal blend, testing and measurement must be updated accordingly. However, such testing is performed offline, which is time consuming and costly.

Accordingly, the apparatus and method of the present disclosure may generate an IDT predictive model to predict coal IDT without a separate offline test.

Referring to FIG. 1, an apparatus 100 for predicting deformation temperature of coal using the IDT predictive model may include a parameter extractor 110, a temperature analyzer 120, a modeler 130, and a predictor 140.

The parameter extractor 110 may be configured to analyze the characteristics of the test coal and extract (or derive) a plurality of parameters from the analysis result, where the plurality of parameters represent the characteristics of the test coal. Here, the test coal may refer to coal used to generate the IDT predictive model. The parameter extractor 110 may analyze the characteristics of the test coal through ash component analysis, elementary analysis, industrial analysis, or calorific value analysis.

Elementary analysis may be performed by the parameter extractor 110 to derive the element content that oxidizes, decomposes, and reduces specific elements generated when the test coal is burned. Here, the specific element may include carbon (C), hydrogen (H), nitrogen (N), oxygen (O), sulfur (S), or ash, and the content may be expressed as a weight ratio. In an embodiment, the weight ratio may include a mass ratio.

Industrial analysis may be performed by the parameter extractor 110 to derive the degree of weight loss of inherent moisture, ash, volatile matter, fixed carbon, and the like.

Ash component analysis may be performed by the parameter extractor 110 to derive the content of coal ash (ash component) present in test coal. Here, the ash component may include oxides such as iron oxide (FeO) titanium dioxide ($TiO_2$), phosphorus pentoxide ($P_2O_5$), calcium oxide (CaO), magnesium oxide (MgO), sodium oxide ($Na_2O$), or potassium oxide ($K_2O$), and the content may be expressed as a weight ratio. In an embodiment, the weight ratio may include a mass ratio.

In addition, the parameter extractor 110 may extract a plurality of parameters representing the characteristics of the test coal from the analyzed result of the characteristics of the test coal. For example, through ash component analysis, the parameter extractor 110 may extract the content of at least one of $SiO_2$, $Al_2O_3$, CaO, MgO, $Na_2O$, $K_2O$, $TiO_2$, and $SO_3$ as a parameter.

In addition, the parameter extractor 110 may generate derived parameters by combining a plurality of extracted parameters according to the relationship between the extracted parameters. For example, the parameter extractor 110 may combine the $SiO_2$ and $Al_2O_3$ content among the extracted components of $SiO_2$, $Al_2O_3$, CaO, MgO, $Na_2O$, $K_2O$, $TiO_2$, and $SO_3$. Since $SiO_2$ and $Al_2O_3$ are a combination having a positive correlation with an initial deformation temperature (IDT) of the test coal, that is, the test coal IDT, the parameter extractor 110 may generate the sum of $SiO_2$ content and $Al_2O_3$ content as a derivative parameter. As an alternative, the parameter extractor 110 may combine the CaO and MgO content among the extracted components. In this case, since CaO and MgO are a combination indicating a large impact on the melting point of the test coal, the parameter extractor 110 may generate the sum of CaO content and MgO content as a derivative parameter.

In addition, the parameter extractor 110 may combine basic oxides of $SiO_2$, $Al_2O_3$, CaO, MgO, $Na_2O$, $K_2O$, $TiO_2$, and $SO_3$ extracted through ash component analysis. The basic oxides are a combination representing indices that are comprehensively used to index the melting characteristics of the test coal. The parameter extractor 110 may extract the sum of the contents of the basic oxides as a derivative parameter.

The parameter extractor 110 may be used to generate an initial deformation temperature (IDT) predictive model by introducing a derivative parameter having similar characteristics, in addition to the parameter, and thus a more accurate deformation temperature predictive model may be generated.

The temperature analyzer 120 may analyze the initial deformation temperature of the test coal, that is, the test coal IDT. The test coal IDT may represent the melting point (MP) of ash. The temperature analyzer 120 may analyze the test coal IDT using coal ash fusibility (CAF) or thermomechanical analysis (TMA) methods, or may derive the test coal IDT through image analysis or an analysis of volume in a high temperature furnace. Here, since such measuring or analysis of the test coal IDT may involve high costs, the temperature analyzer 120 may use an initial deformation temperature previously derived through a separate test. That is, the temperature analyzer 120 may store data on the test coal IDT and use the stored data.

The modeler 130 may derive the IDT predictive model using the extracted parameters and the test coal IDT. Specifically, the modeler 130 may model the plurality of parameters and the test coal IDT through machine learning. Here, the modeler 130 may derive the IDT predictive model based on the relationship between the initial deformation temperature and the plurality of parameters extracted by the parameter extractor 110. The modeler 130 may learn the IDT predictive model by using a repeated k-fold cross-validation method. The IDT predictive model derived from the modeler 130 may input a parameter of coal as an input value and output the initial deformation temperature (IDT) of coal as an output value.

The predictor 140 may predict the initial deformation temperature for the characteristics of the target coal by substituting the characteristics of the target coal into the IDT predictive model. The predictor 140 may predict the initial deformation temperature by using the characteristics and parameters of the target coal as input values of the IDT predictive model. The predictor 140 may predict the initial deformation temperature of the target coal, that is, the target coal IDT, using the output value of the IDT predictive model obtained when the characteristics and parameters of the target coal are input values.

Figure 2:
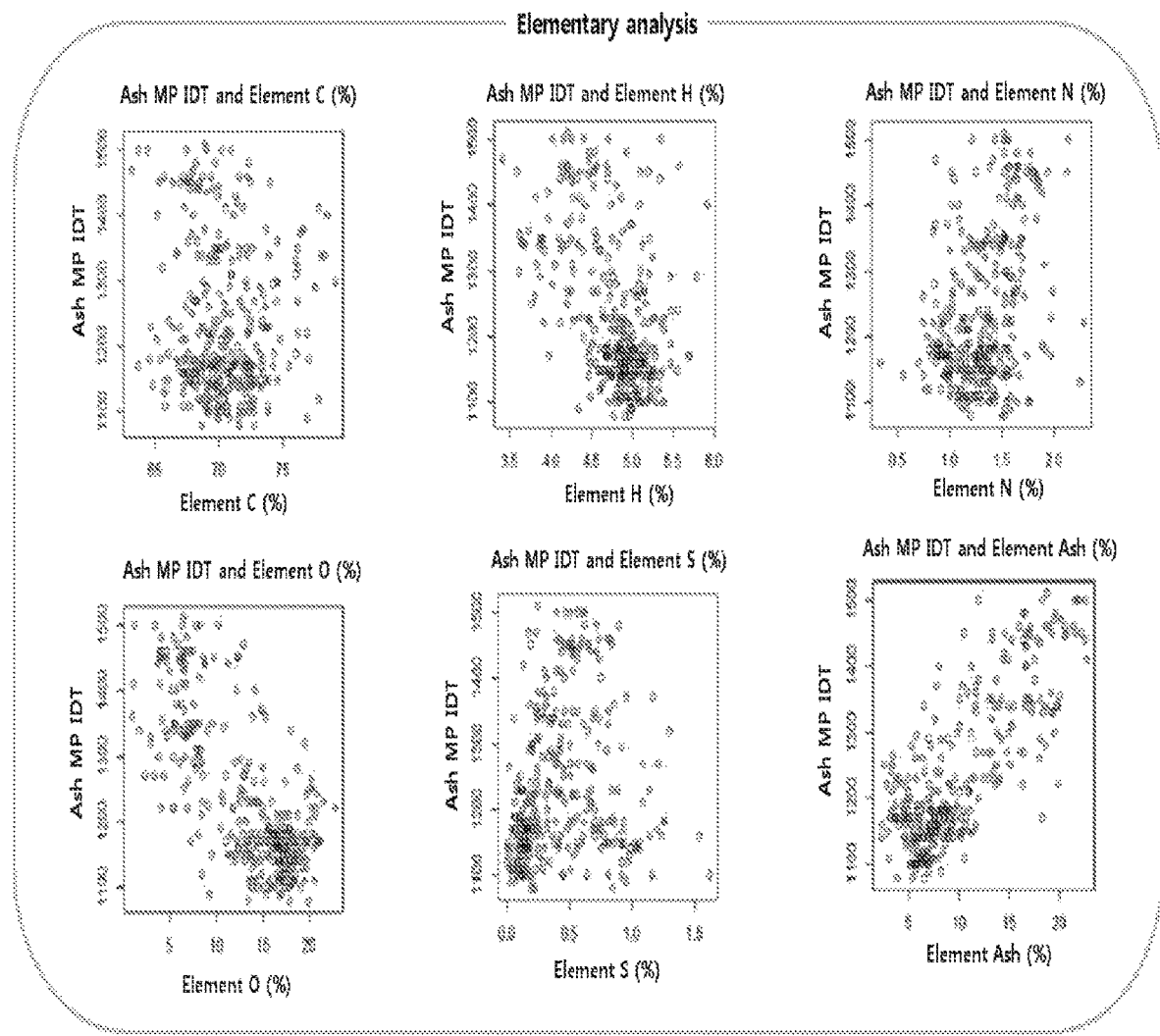
FIG. 2 is a set of elementary analysis results showing the characteristics of test coal for each of six elements according to an embodiment of the present disclosure.

FIG. 2 shows elementary analysis results for the characteristics of test coal for each of six elements, respectively.

Referring to FIG. 2, the parameter extractor 110 may extract the characteristics of coal. Analytical methods for extracting the characteristics of coal may include elementary analysis, industrial analysis, sulfur analysis, and calorific value analysis. The elementary analysis is to derive the content of element generated when the coal is burned. The parameter extractor 110 may derive the content of carbon (C), hydrogen (H), nitrogen (N), oxygen (O), sulfur (S), and ash generated when the test coal is burned. The parameter extractor 110 may derive the content of elements from a plurality of test coal samples.

In addition, the temperature analyzer 120 may analyze the initial deformation temperature according to characteristics of the test coal samples. The temperature analyzer 120 may analyze the initial deformation temperature according to the element content of the plurality of test coal samples. For example, the parameter extractor 110 may extract 70% of the content of carbon generated when the test coal is burned, and the temperature analyzer 120 may analyze that the initial deformation temperature having the carbon content of 70% corresponds to 1100° C.

Figure 3:
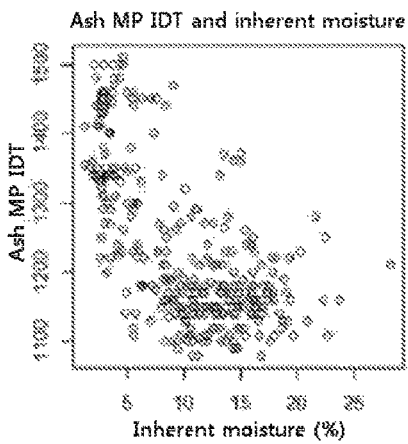
FIG. 3 is a set of industrial analysis results showing the characteristics of test coal for each of four parameters according to an embodiment of the present disclosure.
Figure 3:
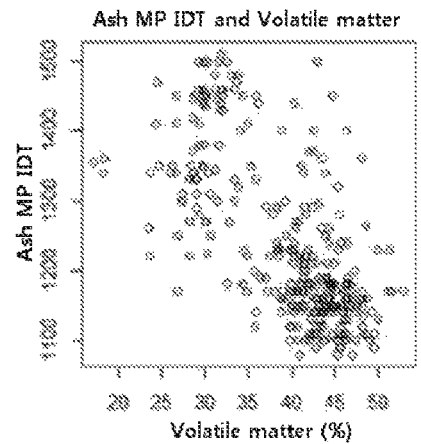
Figure 3:
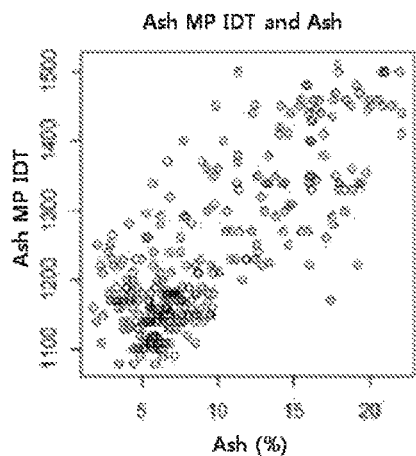
Figure 3:
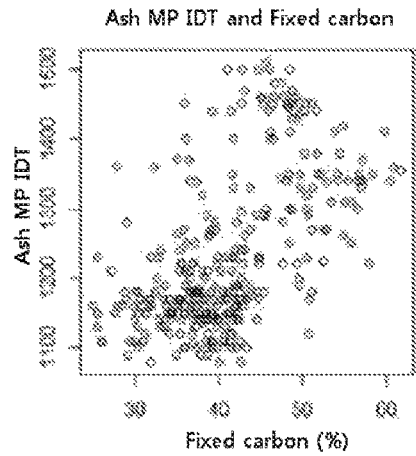

FIG. 3 shows industrial analysis results for the characteristics of test coal for each of four parameters, respectively.

Referring to FIG. 3, the parameter extractor 110 may extract the characteristics of coal. Analytical methods for extracting the characteristics of coal may include elementary analysis, industrial analysis, sulfur analysis, and calorific value analysis. The industrial analysis is to dry some of the coal materials to derive degree of weight loss. The parameter extractor 110 may derive the degree of weight loss by drying inherent moisture, volatile matter, ash, fixed carbon, and the like. That is, the parameter extractor 110 can derive how much the weight of inherent moisture, volatile matter, ash, and fixed carbon is reduced after drying, compared to corresponding weights before drying. The parameter extractor 110 may derive the degree of weight loss of inherent moisture, volatile matter, ash, and fixed carbon from a plurality of test coal samples.

In addition, the temperature analyzer 120 may analyze the initial deformation temperature according to characteristics of the test coal samples. The temperature analyzer 120 may analyze the deformation temperature according to the degree of weight loss of moisture, volatile matter, ash, and fixed carbon of the plurality of test coal samples. For example, the parameter extractor 110 may extract that the weight loss ratio of water is 15%, and the temperature analyzer 120 may analyze that the deformation temperature having 15% weight loss ratio of water corresponds to 1100° C.

Figure 4:
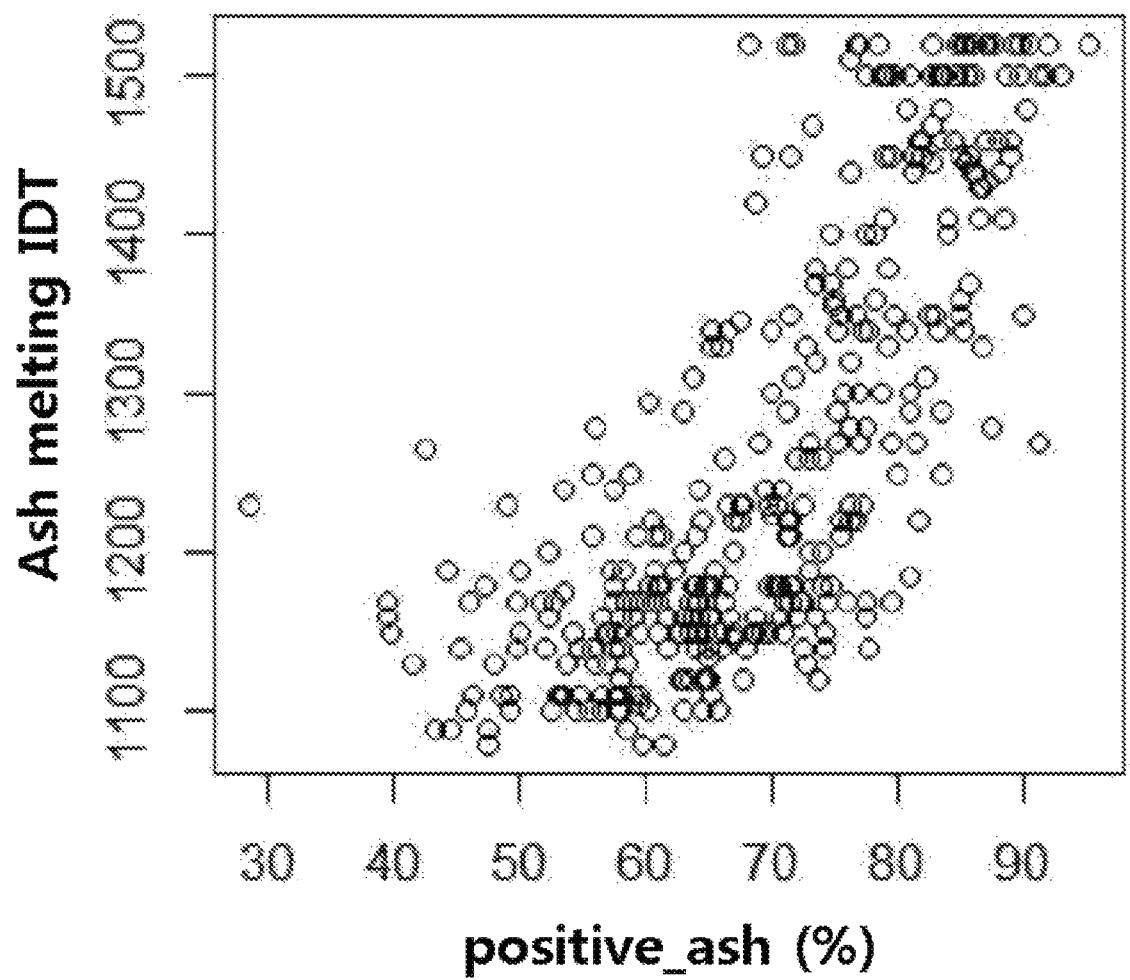
FIGS. 4-6 are diagrams illustrating extraction of derived parameters by ash component analysis according to embodiments of the present disclosure, respectively.
Figure 5:
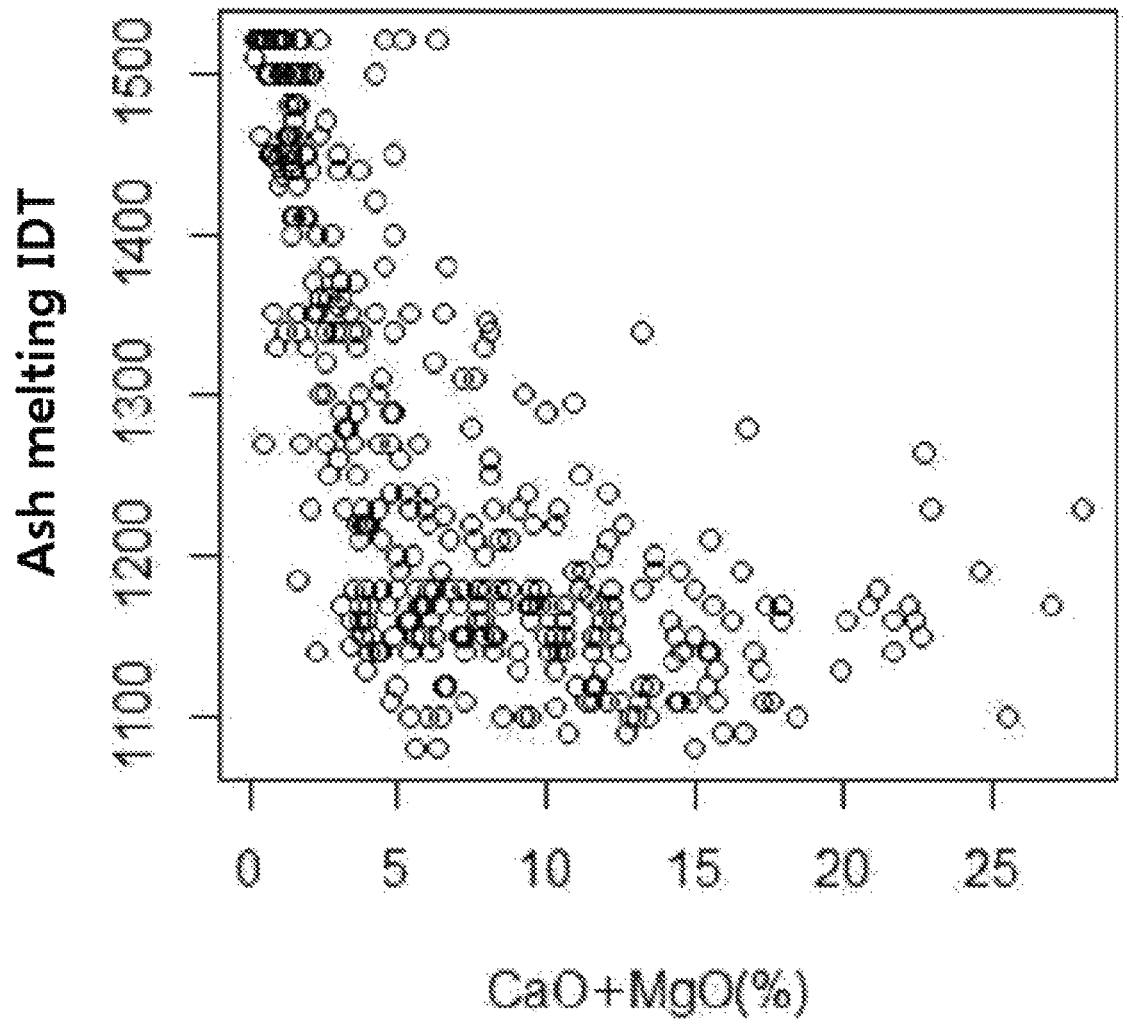
Figure 6:
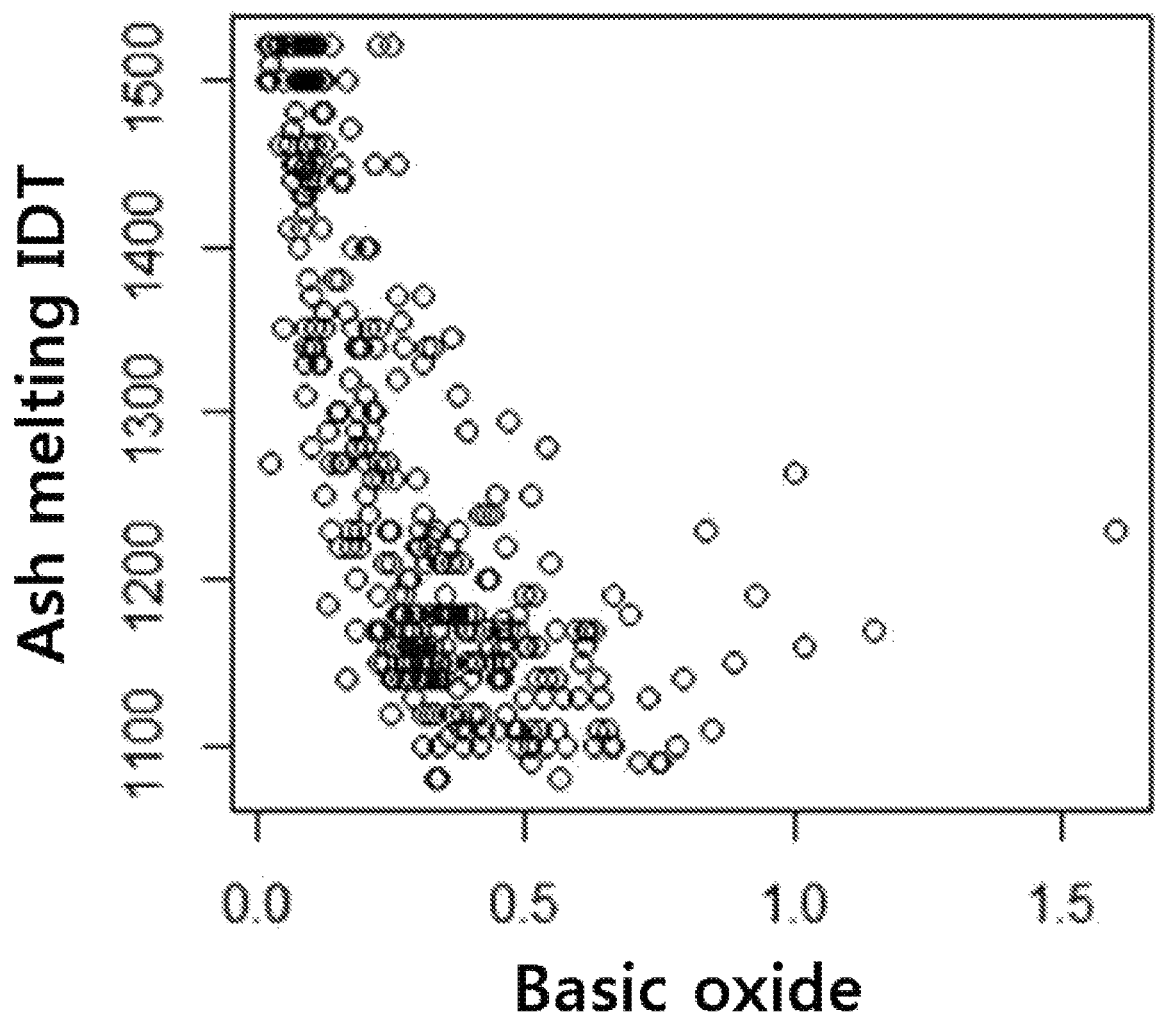

FIGS. 4-6 illustrate extraction of derived parameters by ash component analysis according to embodiments of the present disclosure.

Referring to FIG. 4, the parameter extractor 110 may extract parameters based on the characteristics of the test coal extracted through ash component analysis. Here, the parameters extracted by the parameter extractor 110 may be the content of $SiO_2$, $Al_2O_3$, $CaO$, $MgO$, $Na_2O$, $K_2O$, $TiO_2$, and $SO_3$. The parameter extractor 110 may generate derivative parameters by combining the parameters according to the relationship of these parameters.

The parameter extractor 110 may combine parameters having a positive correlation with the test coal IDT. $SiO_2$ and $Al_2O_3$ among $SiO_2$, $Al_2O_3$, $CaO$, $MgO$, $Na_2O$, $K_2O$, $TiO_2$, and $SO_3$ extracted by the parameter extractor 110 may have a positive correlation with the test coal IDT. Thus, the parameter extractor 110 may generate, as a derivative parameter, the sum of the content of $SiO_2$ and $Al_2O_3$ having a positive correlation with the test coal IDT, among $SiO_2$, $Al_2O_3$, $CaO$, $MgO$, $Na_2O$, $K_2O$, $TiO_2$, and $SO_3$.

Referring to FIG. 5, the parameter extractor 110 may extract parameters based on the characteristics of the test coal extracted through ash component analysis. Here, the parameters extracted by the parameter extractor 110 may be the content of $SiO_2$, $Al_2O_3$, $CaO$, $MgO$, $Na_2O$, $K_2O$, $TiO_2$, and $SO_3$. The parameter extractor 110 may generate derivative parameters by combining the parameters according to the relationship of these parameters.

The parameter extractor 110 may combine parameters that greatly impact the melting of the test coal. The content of $CaO$ and $MgO$, among $SiO_2$, $Al_2O_3$, $CaO$, $MgO$, $Na_2O$, $K_2O$, $TiO_2$, and $SO_3$, extracted by the parameter extractor 110, may have a great impact on the melting of the test coal. Thus, the parameter extractor 110 may generate, as a derivative parameter, the sum of the content of $CaO$ and $MgO$ having a great impact on the melting of the test coal, among $SiO_2$, $Al_2O_3$, $CaO$, $MgO$, $Na_2O$, $K_2O$, $TiO_2$, and $SO_3$.

Referring to FIG. 6, the parameter extractor 110 may extract parameters based on the characteristics of the test coal extracted through ash component analysis. Here, the parameters extracted by the parameter extractor 110 may be the content of $SiO_2$, $Al_2O_3$, $CaO$, $MgO$, $Na_2O$, $K_2O$, $TiO_2$, and $SO_3$. The parameter extractor 110 may generate derivative parameters by combining the parameters according to the relationship of these parameters.

The parameter extractor 110 may combine basic oxides. The parameter extractor 110 may generate, as a derivative parameter, the sum of basic oxides among $SiO_2$, $Al_2O_3$, $CaO$, $MgO$, $Na_2O$, $K_2O$, $TiO_2$, and $SO_3$. The basic oxides may be comprehensively used to index the melting characteristics of the test coal.

Figure 7:
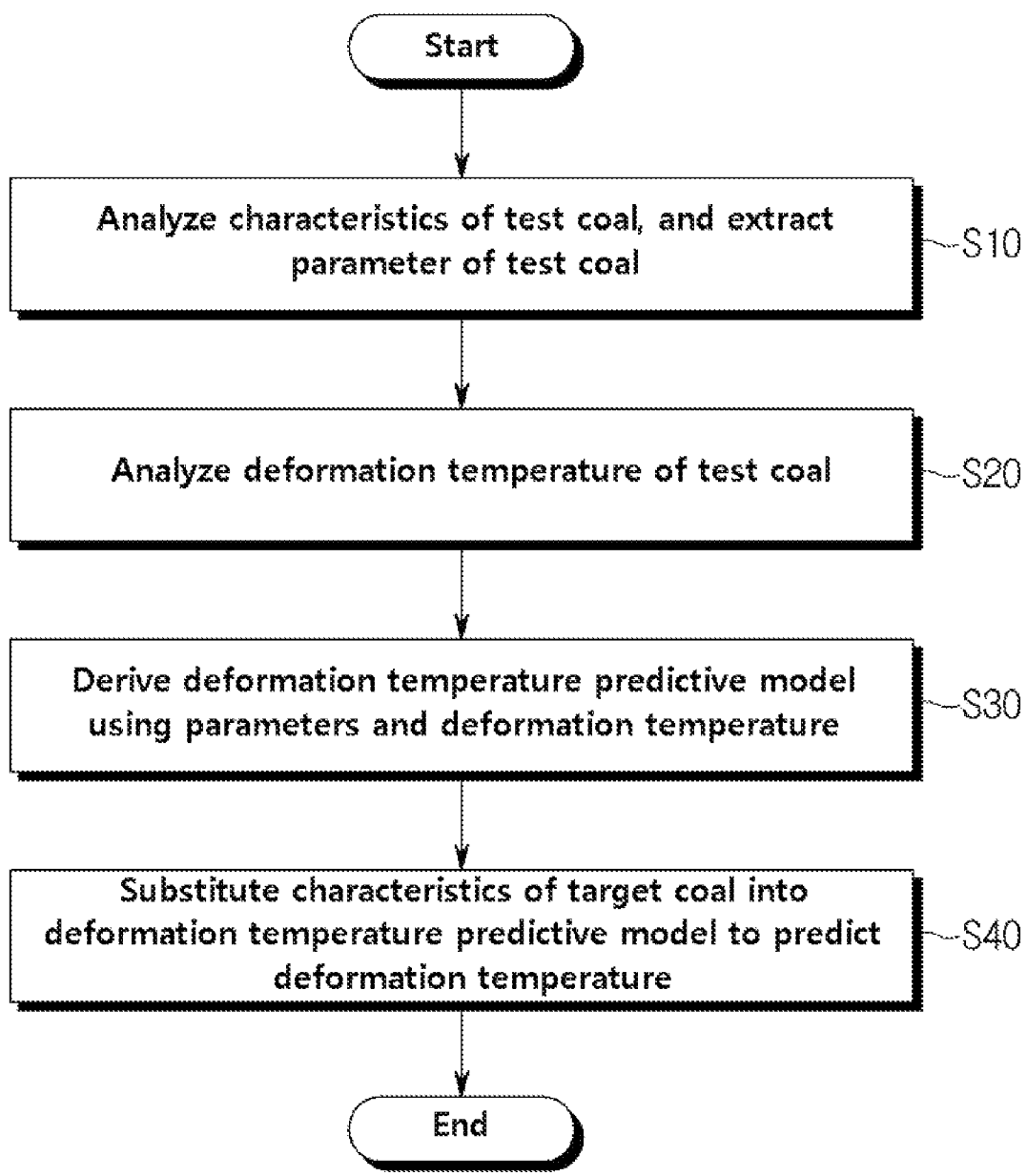
FIG. 7 is a flowchart of a method for predicting initial deformation temperature of coal according to an embodiment of the present disclosure.

FIG. 7 illustrates a method for predicting initial deformation temperature of coal according to an embodiment of the present disclosure.

Referring to FIG. 7, the parameter extractor 110 may analyze the characteristics of the test coal and extract a plurality of parameters of the test coal from the analysis result (S10). Here, the test coal may refer to coal used to generate the IDT predictive model. The parameter extractor 110 may analyze the characteristics of the test coal through ash component analysis, elementary analysis, industrial analysis, or calorific value analysis. In addition, the parameter extractor 110 may extract parameters representing the characteristics of the coal.

The temperature analyzer 120 may analyze the test coal IDT (S20). Here, the temperature analyzer 120 may analyze the test coal IDT based on the characteristics and parameters of the coal extracted by the parameter extractor 110. That is, the temperature analyzer 120 may analyze the initial deformation temperature of the coal with respect to the characteristics of the coal.

The modeler 130 may derive the IDT predictive model using the extracted parameters and the test coal IDT (S30). Specifically, the modeler 130 may model the plurality of parameters and the test coal IDT through machine learning. Here, the modeler 130 may derive the IDT predictive model based on the relationship between the initial deformation temperature and the plurality of parameters extracted by the parameter extractor 110. The modeler 130 may learn the IDT predictive model by using a repeated k-fold cross-validation method. The IDT predictive model derived from the modeler 130 may input a parameter of coal as an input value and output the initial deformation temperature of coal as an output value.

The predictor 140 may predict the initial deformation temperature according to characteristics of the target coal by substituting the characteristics of the target coal into the IDT predictive model (S40). The predictor 140 may predict the initial deformation temperature by using the characteristics and parameters of the target coal as input values of the IDT predictive model. The predictor 140 may predict the target coal IDT using the output value of the IDT predictive model obtained when the characteristics and parameters of the target coal are input values.

As set forth in the foregoing, according to the present disclosure, there is provided an apparatus and method whereby an initial deformation temperature according to characteristics of coal is predicted by deriving a predictive model for the initial deformation temperature (IDT predictive model) and putting the characteristics of coal into the IDT predictive model to predict the initial deformation temperature without a separate test.

According to the present disclosure, the method of predicting the initial deformation temperature of coal may be implemented as a computer program that can be stored in a computer-readable storage medium. Here, the computer program may include a set of instructions for performing the method of FIG. 7 as described above.

As those skilled in the art to which the present disclosure pertains may implement the present disclosure in other specific forms without changing the technical spirit or essential features, the embodiments described above should be understood as illustrative and not restrictive in all respects. The scope of the present disclosure is indicated by the appended claims rather than the detailed description, and all changes or modifications derived from the meaning and scope of the claims and their equivalents should be construed as being included in the scope of the present disclosure.

The invention claimed is:

1. An apparatus for predicting an initial deformation temperature (IDT) of coal consumed in a coal-fired power plant, the apparatus comprising:
   a parameter extractor configured to analyze characteristics of test coal and to extract parameters of the test coal based on the test coal characteristic analysis, wherein the test coal characteristic analysis comprises industrial analysis which is performed by measuring a weight reduction of inherent moisture, volatile matter, ash, and fixed carbon after drying, compared to corresponding weights before drying;
   a temperature analyzer configured to analyze an initial deformation temperature (IDT) of the test coal;
   a modeler configured to derive an IDT predictive model for predicting the test coal IDT using the extracted parameters of the test coal and the test coal IDT; and
   a predictor configured to predict an initial deformation temperature (IDT) of target coal to be supplied to the coal-fired power plant by substituting parameters of the target coal into the IDT predictive model.

2. The apparatus according to claim 1, wherein the parameter extractor is further configured to analyze the characteristics of the test coal through ash component analysis.

3. The apparatus according to claim 2, wherein the parameters of the test coal extracted through the ash component analysis relate to a content of at least one of $SiO_2$, $Al_2O_3$, $CaO$, $MgO$, $Na_2O$, $K_2O$, $TiO_2$, and $SO_3$.

4. The apparatus according to claim 3,
   wherein the parameter extractor is further configured to generate a derivative parameter by combining the extracted parameters of the test coal depending on a correlation with the test coal IDT, and
   wherein the modeler is further configured to derive the IDT predictive model by using the parameters of the test coal, the test coal IDT, and the derivative parameters.

5. The apparatus according to claim 4, wherein the parameter extractor is further configured to generate the derivative parameter as a sum of $SiO_2$ content and $Al_2O_3$ content.

6. The apparatus according to claim 4, wherein the parameter extractor is further configured to generate the derivative parameter as a sum of $CaO$ content and $MgO$ content.

7. The apparatus according to claim 4, wherein the parameter extractor is further configured to generate the derivative parameter as a sum of contents of basic oxides.

8. The apparatus according to claim 1, wherein the modeler is further configured to model parameters of the test coal and the test coal IDT through machine learning.

9. The apparatus according to claim 1, wherein the predictor is further configured to analyze the characteristics of the target coal and to extract the parameters of the target coal based on the target coal characteristic analysis.

10. A method of predicting an initial deformation temperature (IDT) of coal consumed in a coal-fired power plant, the method comprising:
   analyzing characteristics of test coal;
   extracting parameters of the test coal based on the test coal characteristic analysis, wherein the test coal characteristic analysis comprises industrial analysis which is performed by measuring a weight reduction of inherent moisture, volatile matter, ash, and fixed carbon after drying, compared to corresponding weights before drying;

analyzing an initial deformation temperature (IDT) of the test coal;

deriving an IDT predictive model for predicting the test coal IDT using the extracted parameters of the test coal and the test coal IDT; and predicting an initial deformation temperature (IDT) of target coal to be supplied to the coal-fired power plant by using parameters of the target coal in the IDT predictive model.

11. The method according to claim 10, wherein the characteristics of the test coal are analyzed through ash component analysis.

12. The method according to claim 11, wherein the parameters of the test coal extracted through the ash component analysis relate to a content of at least one of $SiO_2$, $Al_2O_3$, CaO, MgO, $Na_2O$, $K_2O$, $TiO_2$, and $SO_3$.

13. The method according to claim 12, further comprising:

generating a derivative parameter by combining the extracted parameters of the test coal depending on a correlation with the test coal IDT, wherein the IDT predictive model is derived by using all of the parameters of the test coal, the test coal IDT, and the derivative parameters.

14. The method according to claim 13, wherein the derivative parameter is generated as a sum of $SiO_2$ content and $Al_2O_3$ content.

15. The method according to claim 13, wherein the derivative parameter is generated as a sum of CaO content and MgO content.

16. The method according to claim 13, wherein the derivative parameter is generated as a sum of contents of basic oxides.

17. The method according to claim 10, wherein the IDT predictive model is derived by modeling the parameters of the test coal and the test coal IDT through machine learning.

18. The method according to claim 10, wherein the target coal IDT predicting comprises:

analyzing the characteristics of the target coal; and extracting parameters of the target coal based on the target coal characteristic analysis.

19. A non-transitory computer readable storage medium storing a computer program comprising instructions for performing the method according to claim 10.

* * * * *